(12) United States Patent
Puskas

(10) Patent No.: US 9,675,747 B2
(45) Date of Patent: Jun. 13, 2017

(54) METHODS AND SYSTEMS FOR IMPROVED CAVITATION EFFICIENCY AND DENSITY, CANCER CELL DESTRUCTION, AND/OR CAUSING A TARGET OBJECT TO BE A CAVITATION NUCLEUS

(71) Applicant: William L Puskas, New London, NH (US)

(72) Inventor: William L Puskas, New London, NH (US)

(*) Notice: Subject to any disclaimer, the term of this patent is extended or adjusted under 35 U.S.C. 154(b) by 0 days.

(21) Appl. No.: 13/961,832

(22) Filed: Aug. 7, 2013

(65) Prior Publication Data

US 2014/0272929 A1     Sep. 18, 2014

Related U.S. Application Data

(60) Provisional application No. 61/786,827, filed on Mar. 15, 2013.

(51) Int. Cl.
| | |
|---|---|
| *A61M 1/36* | (2006.01) |
| *C12N 13/00* | (2006.01) |
| *C12N 1/06* | (2006.01) |

(52) U.S. Cl.
CPC ............ *A61M 1/36* (2013.01); *A61M 1/3621* (2013.01); *A61M 1/3678* (2014.02); *C12N 1/066* (2013.01); *C12N 13/00* (2013.01); *A61M 2205/3375* (2013.01)

(58) Field of Classification Search
CPC .... A61L 2/00; A61L 2/02; A61L 2/025; B01J 19/00; B01J 19/08; B01J 19/10; A61M 1/36; A61M 1/3678; A61M 1/3621; A61M 2205/3375; C12N 1/066; C12N 13/00

USPC .......................................... 422/20; 604/4.01
See application file for complete search history.

(56) References Cited

U.S. PATENT DOCUMENTS

| | | | |
|---|---|---|---|
| 4,315,514 A | 2/1982 | Drewes et al. | |
| 5,401,237 A | 3/1995 | Tachibana et al. | |
| 5,523,058 A * | 6/1996 | Umemura et al. | ............ 422/128 |
| 6,156,549 A * | 12/2000 | Drewes | .................. C12N 13/00 |
| | | | 435/173.7 |
| 6,433,460 B1 | 8/2002 | Puskas | |
| 6,538,360 B2 * | 3/2003 | Puskas | ..................... 310/316.01 |
| 8,518,681 B2 * | 8/2013 | Schafer | ..................... 435/173.7 |
| 2002/0171331 A1 | 11/2002 | Puskas | |
| 2004/0087879 A1 | 5/2004 | Mitragotri et al. | |
| 2006/0058707 A1 | 3/2006 | Barthe et al. | |

(Continued)

OTHER PUBLICATIONS

Data, S., et al., "Ultrasound-Enhanced Thrombolysis Using Definity as a Cavitation Nucleation Agent," Ultrasound in Medicine & Biology, 2008, vol. 34, No. 9, pp. 1421-1433.

(Continued)

*Primary Examiner* — Timothy Cleveland
(74) *Attorney, Agent, or Firm* — Lathrop & Gage LLP

(57) ABSTRACT

A method of causing an object to act as a cavitation nucleus comprising the steps of providing a sound energy source capable of generating a sound energy over a plurality of frequency ranges, providing a target object contained in a liquid, coupling the sound energy source to the liquid, determining a specific frequency range, within the frequency ranges, that resonates the target object, and exposing the target object to sound energy at the specific frequency range to cause the target object to act as a cavitation nucleus.

2 Claims, 19 Drawing Sheets

(56) References Cited

U.S. PATENT DOCUMENTS

| | | | | |
|---|---|---|---|---|
| 2007/0205695 | A1* | 9/2007 | Puskas | 310/317 |
| 2010/0011845 | A1* | 1/2010 | Laugharn et al. | 73/64.53 |
| 2013/0131432 | A1* | 5/2013 | Kline | 600/2 |

OTHER PUBLICATIONS

Miller, D. L., et al., "Lithotripter Shock Waves with Cavitation Nucleation Agents Produce Tumor Growth Reduction and Gene Transfer In Vivo," Ultrasound in Medicine & Biology, 2002, vol. 28, No. 10, pp. 1343-1348.

Xu, Z., et al., "A New Strategy to Enhance Cavitational Tissue Erosion Using a High-Intensity, Initiating Sequence," Ultrasonics, Ferroelectrics and Frequency Control, IEEE Transactions, 2006, vol. 53, No. 8, pp. 1412-1424.

PCT Patent Application PCT/US2014/027073 International Search Report and Written Opinion dated Jul. 25, 2014, 11 pages.

International Search Report and Written Opinion corresponding to International Patent Application No. PCT/US2016/031677, mailed Aug. 12, 2016, 15 pages.

* cited by examiner

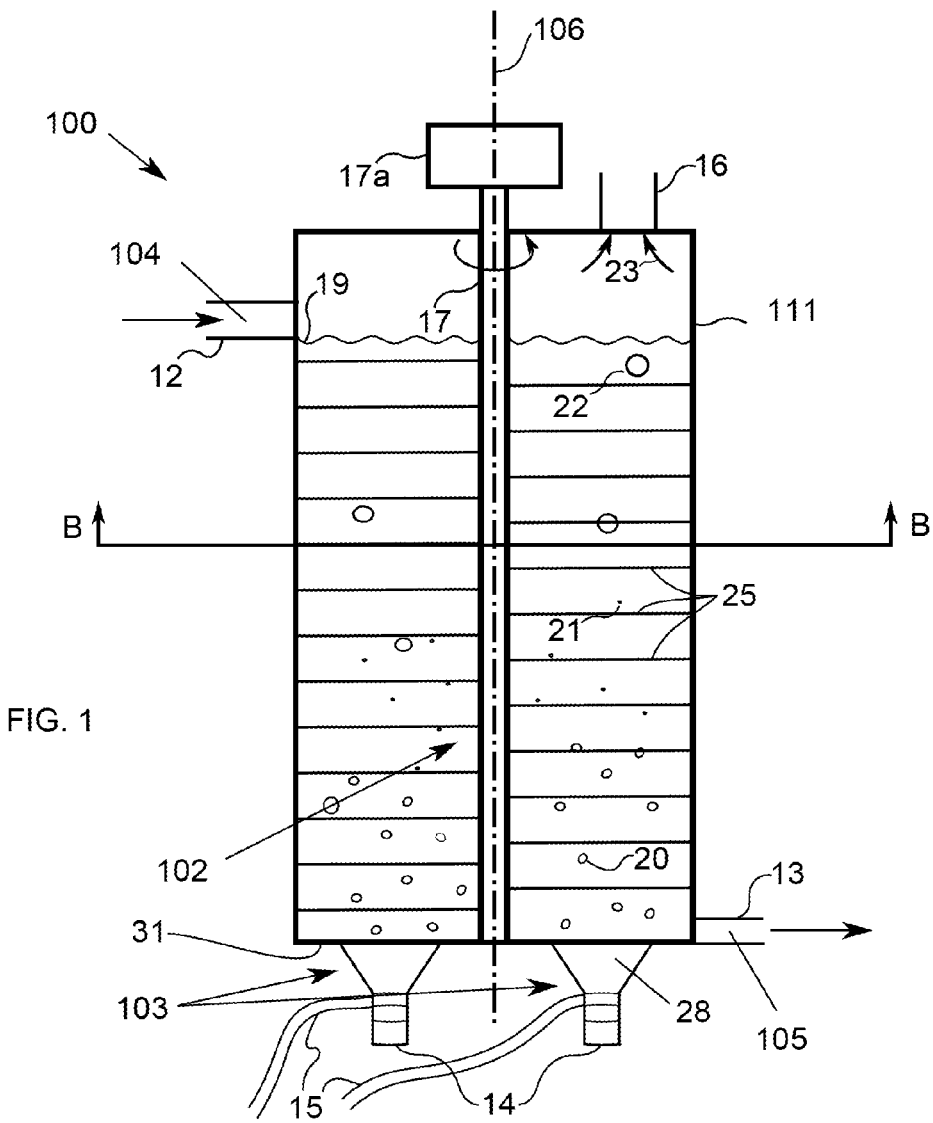
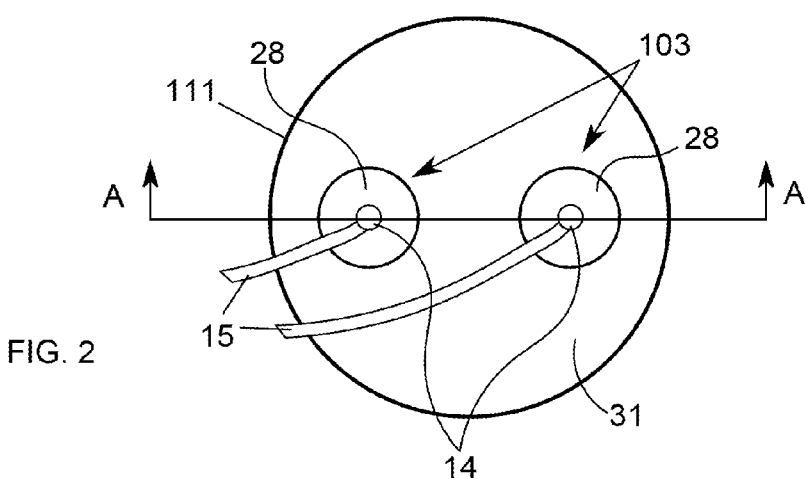
FIG. 1
FIG. 2

PRIOR ART FIG. 9

METHODS AND SYSTEMS FOR IMPROVED CAVITATION EFFICIENCY AND DENSITY, CANCER CELL DESTRUCTION, AND/OR CAUSING A TARGET OBJECT TO BE A CAVITATION NUCLEUS

CROSS-REFERENCE TO RELATED APPLICATIONS

The present application claims the benefit of U.S. Provisional Application No. 61/786,827, entitled "Methods and Systems for Improved Cavitation Efficiency, Organism Deactivation, and/or Causing a Target Object to be a Cavitation Nucleus", and filed Mar. 15, 2013; which is hereby incorporated by reference in its entirety.

TECHNICAL FIELD

The present invention relates to sonic, ultrasonic and megasonic systems, and more particularly to systems and methods for generating acoustic cavitation events in liquid media for applications such as cleaning, sonochemistry, and inactivating or destroying microorganisms, cells, and other organisms.

BACKGROUND ART

For years, energy in the form of sonic, ultrasonic and megasonic waves has been transmitted into liquid media for purposes such as: to process the liquid media, to inactivate organisms within the liquid media, to enhance chemical reactions (sonochemistry), to degas the liquid media and to clean objects within the liquid media. It is well known that objects may be efficiently cleaned or processed by immersion in a liquid and subsequent application of ultrasonic or megasonic energy to the liquid. It is also well known that liquids can be emulsified, homogenized, mixed and/or degased by application of ultrasonic or megasonic energy to the liquid. Applications such as inactivation of organisms, pasteurization, and sterilization are documented in the ultrasonic literature.

For example, U.S. Pat. No. 7,726,325 is directed to a de-aeration device and ultrasonic cleaning device. International patent application no. WO2008/007631 is directed to a fine bubble generating unit. U.S. Pat. App. No. 2010/0175791 is directed to a super-micro bubble generation device. U.S. Pat. App. No. 2012/0282384 is directed to a fine bubble generating apparatus. The article entitled "Development of Functional Microbubbles for Ultrasound Therapy", in the Proceedings of the 8th International Symposium on Cavitation, Aug. 13-16, 2012 is directed to a method of creating micro bubbles using shear flow. The article "Microbubble ultrasound contrast agents: a review", by Stride, et. al., in Proc. Instn Mech. Engrs. Vol. 217, 2003, provides a review of ultrasound contrast agents. The journal article entitled "Potential uses of ultrasound in the biological decontamination of water", by Mason et al., from the Ultrasonics Sonochemistry (vol. 10 (2003) p. 319-323) discusses using ultrasound to kill bacteria and other microorganisms. U.S. Pat. No. 6,960,173 is directed to an ultrasound wound treatment method and device using standing waves. The article entitled "Inactivation of microbes using ultrasound: a review", by Piyasena, et al., and published in the International Journal of Food Microbiology (vol. 87 (2003) p. 207-216) discusses juice pasteurization with ultrasound. In the article entitled "A review of research into the uses of low level ultrasound in cancer therapy", by Yu, et. al., in Ultrasonics Sonochemistry (vol. 11 (2004) p. 95-103), the use of ultrasound is discussed in the treatment of cancer. U.S. Pat. App. No. 2012/0291765 is directed to an apparatus for heating fluids for pre-treating hydraulic fracturing water through passing the fluid through a device with a spinning disk. The discussion of the above references is merely for reference and no assertion is made that the above references are in the same field of the invention or are valid prior art.

BRIEF SUMMARY OF THE INVENTION

With parenthetical reference to the corresponding parts, portions or surfaces of the disclosed embodiment, merely for the purposes of illustration and not by way of limitation, provided is a method of causing an object to act as a cavitation nucleus comprising the steps of: providing a sound energy source capable of generating a sound energy over a plurality of frequency ranges; providing a target object contained in a liquid; coupling the sound energy source to the liquid; and exposing the target object to sound energy at the specific frequency range to cause the target object to act as a cavitation nucleus.

In another aspect, provided is a method of causing an object to act as a cavitation nucleus comprising the steps of providing a target object contained in a liquid; designing and building a sound energy source with a specific frequency range that resonates the target object; coupling the sound energy source to the liquid; and exposing the target object to sound energy at the specific frequency range to cause the target object to act as a cavitation nucleus.

In another aspect, provided is a method of causing an object to act as a cavitation nucleus comprising the steps of: providing a sound energy source capable of generating a sound energy over a plurality of frequency ranges; providing a target object contained in a liquid; coupling the sound energy source to the liquid; determining a specific frequency range within the frequency ranges that resonate the target object; and exposing the target object to sound energy at the specific frequency range to cause the target object to act as a cavitation nucleus.

The step of determining a specific frequency range may comprise the step of: sequentially exposing a sample of objects equivalent to the target object to different frequency ranges; measuring an effect of sample object resonance after each exposure at a given frequency range; and/or identifying which frequency range has the highest measured effect of resonance.

The measured effect of sample object resonance may comprise a resulting particle count measurement.

The measured effect of target object resonance may have a cell culture inactivation rate measurement.

The inactivation rate measurement may be an exponential rate measurement.

The sound energy source may have a plurality of sound energy producers.

Each sound energy producer may have a transducer capable of generating a different frequency range.

The sound energy source may have a sonic generator and a piezoelectric transducer.

The step of exposing the target object to sound energy may use a second sound energy source.

The method may further have the step of causing the target object to implode.

The cavitation nucleus may be a stably oscillating cavitation nucleus.

The target object may be an organism.

The target object may be a cancer cell.

The target object may be a bacterium.

The target object may be a virus.

The target object is a parasite.

The method may further have the step of providing a tubular vessel having an inlet and an outlet in which the sound energy source is coupled to the vessel.

A plate may be arranged between the vessel and the transducer, and the plate may have a thickness that is approximately or substantially an integer number of half-wavelengths of sound at a center frequency of the specific frequency range.

The piezoelectric transducer may have a piezoelectric ceramic with a thickness that is approximately or substantially an odd integer number of half wavelengths of sound at the center frequency of the specific frequency range.

The step of determining a specific frequency range may have the step of conducting a cell culture on a set of controlled samples, and each sample may be exposed to sound energy at different frequency ranges.

The step of determining a specific frequency range may have the step of measuring a particle count on a set of controlled samples, and each sample may be exposed to sound energy at a different frequency range.

The generator may be a sweeping frequency megasonic generator having a center frequency in the range 350 kHz to 15 MHz and having a sweep frequency bandwidth between 0.1 percent and 7 percent of the megasonic center frequency.

The transducer may be a piezoelectric megasonic transducer bonded to a plate coupled to the liquid, and the megasonic transducer may have a center frequency in the range 350 kHz to 15 MHz and may have a thickness of piezoelectric transducer material approximately or substantially equal to an odd integer number of half wavelengths of sound at the center frequency and/or a plate thickness approximately or substantially equal to an integer number of half wavelengths of the center frequency.

In another aspect, provided is a method of causing a cell to act as a cavitation nucleus having the steps of: providing a target cell contained in a liquid; designing and building a sound energy source with a specific frequency range that resonates said target object; exposing the target cell in the liquid to sound energy at the specific frequency range to cause the target cell to act as a cavitation nucleus; whereby the target cell is inactivated.

In another aspect, provided is a method of causing a cell to act as a cavitation nucleus having the steps of: providing a sound energy source capable of generating a sound energy over a plurality of frequency ranges; providing multiple test sets of cells in a liquid; exposing each test set of cells to sound energy at a different frequency range; determining an inactivation efficiency for each test set; determining an optimal frequency range out of the frequency ranges which has the highest inactivation efficiency; providing a target cell contained in a liquid; exposing the target cell in the liquid to sound energy at the optimal frequency range to cause the target cell to act as a cavitation nucleus; whereby the target cell is inactivated.

The inactivation efficiency may include a measure of an exponential rate of decrease in the number of active cells remaining.

In another aspect, provided is an apparatus for destroying cancer cells in blood having: a first catheter for receiving a blood flow from a body; a blood pump; a vessel through which the blood flow passes and having a sound energy source, the sound energy source configured and arranged to generate sound energy having a frequency range that causes the cancer cells to become cavitation nuclei; and a second catheter for returning the blood flow to the body.

The vessel may have a megasonic transducer coupled to a megasonic generator.

The frequency range may be selected to discourage non-cancerous cells from becoming cavitation nuclei.

In another aspect, provided is an apparatus for treating a liquid for sonic applications having: a vessel for holding a portion of the liquid having a sound energy source configured and arranged to cause a gas in the liquid to form into bubbles; a cutting system for cutting the bubbles having: a cutting element configured and arranged for relative motion to a portion of the liquid, in which the apparatus is configured and arranged to cause the bubbles to be cut into a size for improved cavitation efficiency in the liquid.

The vessel further may have a liquid inlet, and/or a liquid outlet.

The vessel further may have a gas outlet.

The sound energy source may be immersed within the vessel or bonded to a wall of the vessel.

The sonic generator may have a sonic frequency between 18 kHz and 350 kHz.

The sonic generator may have a sonic frequency between 350 kHz and 15 MHz.

The sonic generator may have a variable frequency configured and arranged to sweep through a specified frequency range.

The sound energy source may have a piezoelectric transducer.

The cutting element may be a blade, wire, or string.

The cutting element may be stationary and a portion of the fluid may be passed by the cutting element.

The cutting system may have a rotating shaft holding the cutting element and a rotary motor may be configured and arranged to drive the shaft relative to the vessel.

The blade system is configured and arranged to cut the bubble size to a size which does not cause or promote conversion of sonic energy from the sound energy source directly into heat.

The apparatus may further comprising a second vessel coupled to the first vessel.

The sound energy source and the blade cutting system may be arranged at the first vessel, and/or the second vessel may have a sonic processing system.

The apparatus may further comprise a third vessel arranged between the first vessel and the second vessel, and for holding fluid processed by the first vessel before being passed into the second vessel.

The apparatus may further have a recirculation path between the liquid outlet and liquid inlet.

The apparatus may further have one or more transducers.

The liquid may have, a body fluid, a hydraulic fracturing fluid, and/or a food.

The body fluid may be blood or interstitial fluid.

The food may be a fruit juice.

The apparatus may be configured for continuous operation.

The apparatus may be configured for batch processing.

In another aspect, provided is a method of conditioning a liquid for sonic applications having the steps of: providing a liquid with a gas content; providing a sound energy source; providing a cutting system; coupling the sound energy source to the liquid to cause bubbles to form; and cutting a portion of the bubbles with the cutting system to cause the bubbles to have a different bubble population size profile.

The cutting system may have a cutting element, the cutting element having a blade, wire, or string.

The cutting system may have a rotary motor configured and arranged to rotate the cutting element relative to the liquid.

The sound energy source may be a piezoelectric transducer.

The sound energy source may be operated at a frequency in the range of 18 kHz to 350 kHz.

The sound energy source may be operated at a frequency in the range of 350 kHz to 15 MHz.

The sound energy source may be operated at a frequency selected to cause a target object of a given diameter to act as a cavitation nucleus.

The method may further have the step of providing a vessel with a liquid inlet and a liquid outlet.

The method may further have the step of providing fluid from the liquid outlet to a sonic apparatus.

The method may further have the step of returning fluid from the sonic apparatus back to the vessel.

The method may operate with a continuous flow.

The method may further have the step of providing a vessel for holding the liquid, and/or the sound energy source may be coupled to the liquid and/or the cutting system may be arranged within the vessel.

The sound energy source may have a sweeping frequency which varies in a predetermined frequency range.

The method may further have the step of providing a target object.

The method may further have the step of physically breaking, shattering, disrupting, inactivating, or destroying the target object.

The liquid may be a body fluid.

The body fluid may be blood, or interstitial fluid.

The liquid may be a food.

The liquid may be a fruit juice.

The liquid may be a hydraulic fracturing fluid.

In another aspect, provided is a method of causing a target object to act as a cavitation nucleus having the steps of: providing a sound energy source; providing a fluid containing the target object; coupling the sound energy source to the fluid; the sound energy source being within a specified frequency range correlated to the target; whereby the target object may be caused to act as a cavitation nucleus.

The target object may be caused to implode.

The cavitation nucleus stably oscillates.

The target object may be an organism.

The target object may be a cancer cell.

The target object may be a bacterium.

The target object may be a virus.

The target object may be a parasite.

The sound energy source may have a sonic generator or a transducer.

The transducer may be a piezoelectric transducer.

The method may further have the step of providing a tubular vessel having an inlet and an outlet.

A plate may be arranged between the vessel and the transducer, the plate having a thickness that may be approximately or substantially an integer number of half-wavelengths of sound at the specified frequency.

The piezoelectric transducer may have a piezoelectric ceramic with a thickness that may be approximately or substantially an odd integer of half wavelengths of sound at the specified frequency.

The tubular vessel may have baffles whereby a fluid path length between the inlet and the outlet may be increased by the baffles.

The tubular vessel may have gas escape tubing for gas released from the liquid.

The method may further include the step of determining the specified frequency range correlated to the target.

The step of determining the specified frequency range may include the step of conducting a cell culture on a set of controlled samples of the target exposed to sonic energy at a set of frequencies.

The step of determining the specified frequency range may include the step of measuring a particle count on a set of controlled samples of the target exposed to sonic energy at a set of frequencies.

In another aspect, provided is an apparatus for destroying cancer cells having: a first catheter for receiving a blood flow from a body; a blood pump; a vessel for holding a portion of the blood flow and having a sound energy source, the sound energy source having a frequency range for causing a cancer cell to become a cavitation nuclei; and a second catheter for returning the blood flow to the body.

The vessel may have a sonic transducer coupled to a sonic generator.

The frequency range may have a center frequency of approximately or substantially 900 kHz.

The apparatus may be configured and arranged to expose the blood flow to the sound energy source for a duration of approximately or substantially 12 seconds.

The frequency range may be configured to discourage non-cancerous cells from becoming cavitation nuclei.

In yet another aspect, the amplitude envelope of the sound energy produced in each of the above described embodiments may be varied in a method to encourage high energy density cavitation events to occur. More specifically, the amplitude of the sound energy produced may be characterized by monotonically increasing amplitude prior to the onset of cavitation. In particular, using a sonic generator which provides an exponentially increasing amplitude is deemed to increase the chances that high energy density cavitation events will occur.

In yet another aspect, the chance of producing high energy events may be further improved by providing a tank or chamber, which may be spherical, where the sonic energy is focused. Such a tank or chamber driven by a sonic generator may also provide a synchronization signal to an additional energy source, for example, an electric current, a neutron source, or a laser or lasers which direct a burst of energy at a cavitation implosion to increase the energy density within the cavitation event.

In yet another aspect, the apparatus may also provide tracking of a three dimensional location and time of a cavitation event in order to allow precise application of additional energy for increasing the energy density of the cavitation event.

In yet another aspect, these improvements can be tuned to produce a single high energy cavitation event in a known location and at a known time or alternatively, the system can be slightly detuned (defocused, for example with either a slight change in frequency or a slight change in the diameter of the chamber) to produce a cloud of multiple high energy cavitation events.

BRIEF DESCRIPTION OF THE DRAWINGS

FIG. 1 shows a side section view of an apparatus of one embodiment for producing conditioned liquid.

FIG. 2 is a bottom view of the apparatus in FIG. 1.

DETAILED DESCRIPTION OF THE PREFERRED EMBODIMENTS

Figure 3:
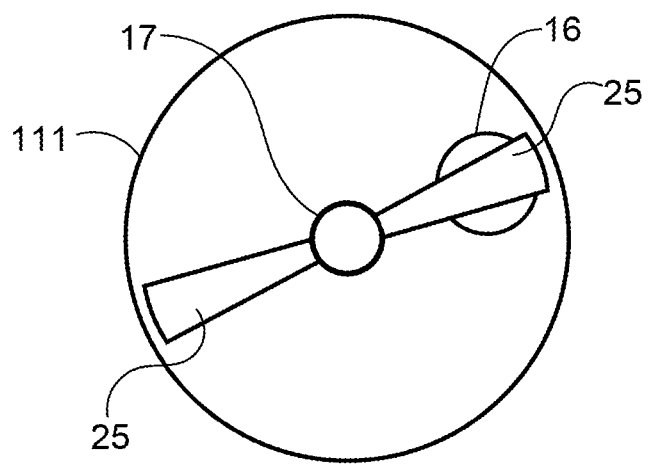
FIG. 3 is a bottom partial section view of the apparatus in FIG. 1.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

Overview

Bubbles in sonically activated liquid are cut into smaller size bubbles by blades, wire, or string to increase the population of bubbles that are the proper size to form a nucleus for cavitations in an ultrasonic or megasonic cleaning or processing apparatus. This results in improved cavitation efficiency for processes such as cleaning, pasteurization and sonochemistry. Organisms, viruses, cells or other target objects in sonically activated liquid are made the nuclei of cavitations by choosing the proper range of frequencies for the sonic activation.

The disclosed embodiments provide a method and system of treating a liquid to cause the liquid to have a bubble population with bubble size characteristics that yield improved cavitation efficiency. More specifically, some of the disclosed embodiments contain a sound energy source for causing dissolved gasses in a liquid to precipitate into bubbles, and a bubble cutting system for causing the bubbles to have a desired size. The disclosed embodiments also provide a method and system for delivering sound energy with a specifically selected frequency profile/range to cause target objects of a given size distribution to act as cavitation nuclei.

Generally, ultrasonic and megasonic systems may include transducers built by bonding piezoelectric ceramics or Langevin assemblies to radiating membranes such as quartz, sapphire, stainless steel, titanium, tantalum, boron nitride, silicon carbide, silicon nitride, aluminum and ceramics, and generators designed to stimulate the transducers at or around a resonant or antiresonant frequency. The transducers are mechanically coupled to a vessel containing a liquid to clean the object of interest or to process the liquid. When the transducers are stimulated by the output signal from the generator to spatially oscillate, they transmit sound waves into the liquid. The interaction between the sound waves and liquid typically produces cavitation and the desired cleaning, degasing, inactivation, destruction, chemical or processing effect.

Some applications, for example, the practical inactivation of microorganisms for pasteurization, have required higher cavitation density than is economically available in state of the art ultrasonic or megasonic systems. The disclosed embodiments provide the ability to generate these required high cavitation densities economically by converting a larger percentage of the available acoustic energy into cavitations. Also, for more common applications such as ultrasonic cleaning, the disclosed embodiments allow the cost of the required equipment to be reduced because the required number of cavitations to accomplish the cleaning application is achieved with less equipment and less energy. More specifically, because of the increased efficiencies provided by the disclosed embodiments, higher power ultrasonic and megasonic systems can be replaced by smaller lower power ultrasonic or megasonic systems.

Some applications, such as pasteurization, require inactivating or destroying all types and sizes of organisms in the liquid. Prior art systems may be available for such applications. However, other applications, such as destroying cancer cells, are best accomplished if specific cells (in this case the cancer cells) are destroyed while leaving other cells of varying size or characteristics unharmed. The disclosed embodiments provide the ability to target cells and/or organisms based upon their size and/or other characteristics, to act as the site of cavitation implosions, while untargeted cells are unlikely to act as the site of cavitation implosions and experience only the more mild effects of a sound wave with a small probability of damage from nearby imploded targeted cells and/or organisms.

This also allows selective organisms, cells or microorganisms to be destroyed while desirable organisms, cells or microorganisms are left unharmed.

Definitions

As used herein, megasonics means sound energy with a fundamental frequency from about 350 kHz to about 15 MHz. As used herein, ultrasonics means sound energy with a fundamental frequency from about 18 kHz to about 350 kHz. The terms sonic, sound waves or sound energy as used herein are defined to mean the complete range of sound waves, including audible, ultrasonic and megasonic frequencies, from about 0.2 kHz to about 15 MHz. As used herein, ultrasound means both ultrasonics and megasonics, with a fundamental frequency from about 18 kHz to about 15 MHz. Although single frequencies are useful in these embodiments, for example, 430 kHz single frequency megasonics, it should be understood that it is common and often an improvement to substitute a range of sweeping frequencies around the single frequency in which case the single frequency is often referred to as the center frequency, although the single frequency can be any frequency in the range, not necessarily the center of the sweep range. For the example of 430 kHz megasonics, the range would typically be about two percent wide, for example 425.7 kHz to 434.3 kHz. For ultrasonic frequencies, the range is typically wider, for example, ten percent. All frequency ranges are dependent on the transducer characteristics and can be less than two percent or greater than ten percent. At a true single frequency, the range is zero percent. Typically the maximum range is less than 20 percent. The sweep function is typically a triangle wave, but many other functions are known, e.g., saw tooth, random frequencies, digital stair step or dual sweep functions. It is implied by any single frequency or frequency range stated in this application or claims that any of the known sweep frequency functions over any sweep frequency range from zero to about 20 percent are substitutes for the single frequency stated or frequency range stated. Conversely, any frequency range stated can have a zero percent range making it the equivalent of a single frequency. Therefore, as used herein, single frequency and frequency range are defined to be the same set of sonic frequency functions.

As used herein, the term "conditioned liquid" is defined to mean a liquid for which bubbles in the liquid have been cut into smaller bubbles.

As used herein, "temperature D-value" refers to decimal reduction time and is the time needed at a certain temperature to kill 90 percent of the organisms of interest, or equivalently, the time to reduce the organism population by one log cycle. As used herein, "frequency D-value" refers to decimal reduction time and is the time needed for exposure to sonic energy at a certain magnitude and frequency (or sweeping frequency range) to kill 90 percent of the organisms of interest, or equivalently, the time to reduce the specific organism population by one log cycle.

As used herein, the word "organism" is defined as the whole range of organic structures, both living and pseudo-living (e.g., viruses). Some examples of the organic structures included in this definition of "organism" are Rhinovirus on the order of 30 nanometers, the bacteria *E. coli* on the order of 2 microns, amoeba on the order of 300 microns and various size cells of both humans and animals.

As used herein, target object includes any organism or microstructure having a size between 5 nanometers and 500 microns.

As used herein, cavitation nuclei and nucleus of cavitation refers to a discontinuity in a liquid that will become a site of transient and/or stable cavitation when sonic parameters are correct, e.g., frequency. Examples of this discontinuity are an organism, an inorganic structure and a gas bubble.

As used herein, the terms 'liquid' and "fluid" are used interchangeably, however, fluids are limited to the liquid form. As used herein, "sound energy producer" includes a physical object which is directly responsible for generating sound energy, for example a transducer, a piezoelectric transducer, a magnetostrictive transducer, piezoelectric ceramic, speaker, or other similar object.

First Embodiment Overview and Structure

Referring now to the drawings and more particularly to FIGS. 1-4, provided is apparatus 100 for creating a liquid that has the characteristic of improved cavitation efficiency when used in an ultrasonic or megasonic cleaning or processing vessel. Apparatus 100 has the major components of vessel 111, bubble cutting system 102, and sound energy source 103. In summary, apparatus 100 receives unconditioned liquid 104, applies a sonic energy from source 103 to cause bubble precipitation, and then cuts the precipitated bubbles with cutting system 102, to create conditioned liquid 105.

FIG. 1 is a side section view taken along section line A-A in bottom view FIG. 2. As shown in FIGS. 1 and 2, vessel 111 has a generally cylindrical shape with central longitudinal axis 106. Vessel 111 has inlet port 12 arranged on its upper left cylindrical side wall as shown in FIG. 1. Inlet port 12 is in fluid communication with a source of unconditioned liquid. Unconditioned liquid 104 passes into vessel 111 through inlet port 12. On vessel 111's bottom right cylindrical side wall is outlet port 13. Conditioned liquid 105 passes out of outlet port 13 and is then provided to another sonic processing apparatus, such as a sonic cleaning apparatus. On the top circular surface of vessel 111 is gas outlet port 16. Excess gas which precipitates from the liquid within vessel 111 passes out of vessel 111 through gas outlet port 16. Arranged on bottom circular surface 31 of vessel 111 is sound energy source 103. Arranged within vessel 111 and centered about axis 106 is cutting system 102.

Figure 4:
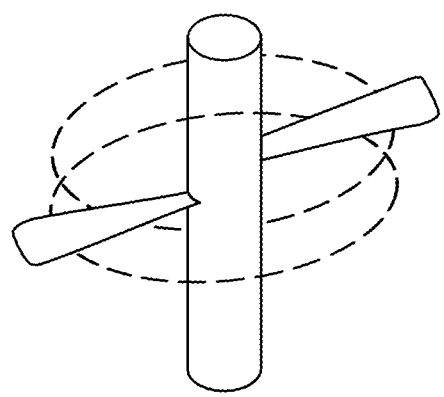
FIG. 4 is a partial perspective view of a portion of the cutting system in FIG. 1.

Cutting system 102 includes rotary motor 17a, motor shaft 17, and a plurality of cutting blades 25. As shown in FIG. 1, rotary motor 17a is mounted near the top circular surface of vessel 111. Rotary motor shaft 17 is arranged with its axis of rotation coincident with vessel longitudinal axis 106. Rotary motor 17a is configured and arranged such that motor shaft 17 rotates relative to vessel 111. Motor shaft 17 extends the entire height of vessel 111. FIG. 3 is a partial bottom view taken along section line B-B in FIG. 1. FIG. 4 is a partial perspective view of a portion of cutting system 102. As shown in FIGS. 1, 3, and 4, cutting blades 25 are generally flat sharp knife-shaped blades oriented radially along shaft 17 with their blade plane parallel to the top and bottom surfaces of vessel 111. However, blades 25 may have a surface plane which is slightly tilted like a propeller to induce a flow through vessel 111. As shown in FIG. 4, blades 25 travel in a circular path about axis 106 through the vessel volume as shaft 17 rotates. Also shown in FIGS. 1 and 4, it can be seen that each blade is offset from the other blades in the direction along the longitudinal axis (i.e. up and down in FIGS. 1 and 4). Motor 17a is capable of rotating cutting blades 25 continuously at a high rate in excess of 5000 rpm, however, motors rotating at significantly lower or higher speeds may also be used. Motor 17a is capable of rotating in both clockwise and counterclockwise directions.

As shown in FIGS. 1 and 2, sound energy source 103 is arranged on the bottom surface 31 of vessel 111. Sound energy source includes transducers 14 which are powered by wires 15. Wires 15 are connected to a sonic generator (not shown in FIG. 1). Transducers 14 are coupled to vessel 111 through front masses 28. The sound energy source is capable of producing sonic energy with a dynamically adjustable frequency in multiple frequency bands within the range of 9 kHz to 15 MHz. The sonic generator and transducers used are the MULTISONIK® system available from Blackstone-NEY Ultrasonics, however other similar sound energy sources including single frequency ultrasound sources may be used.

Unconditioned liquid 104 will ideally have some level of gas dissolved within it. In this embodiment, unconditioned liquid 104, is water, however other similar polar liquids such as ethyl alcohol, or nonpolar liquids, such as benzene, may be used. Inlet port 12 and outlet port 13 can form a recirculation path.

First Embodiment Operation

The operation of apparatus 100 begins with connecting inlet port 12 to a source of unconditioned liquid 104 for filling vessel 111 until the level of liquid in vessel 111 is nearly full, as shown in FIG. 1 at 19. Next, sound energy source 103 is started when an electrical waveform generated by the sonic generator is provided to transducers 14 by wires 15. The sonic energy produced by transducers 14 is coupled to the liquid in vessel 111 through front masses 28 and vessel bottom 31. The sonic energy causes dissolved gasses in the liquid to precipitate in the gas phase, forming small bubbles 20. Some bubbles may begin to rise in vessel 111 due to their buoyancy. Many bubbles will not rise quickly due to their relatively small size in relation to the viscosity of the liquid and the random motion of liquid molecules. Cutting system 102 is started by turning on motor 17a. This causes shaft 17 to rotate and causes blades 25 to rapidly circulate through the liquid and cut larger bubbles 20 into smaller bubbles 21. The direction of rotation of motor 17a is reversed periodically in order to prevent the liquid in vessel 111 from accelerating to rotate at a high speed. Some bubbles (for example 22) may reach upper surface 19 of the liquid and eventually pass out of vessel 111 through gas exit port 16. The combined sonic energy from sound energy source 103 and the cutting of precipitating bubbles by cutting system 102 causes the bubbles in the now conditioned liquid to have a smaller size profile than if there were no cutting system 102.

Figure 5:
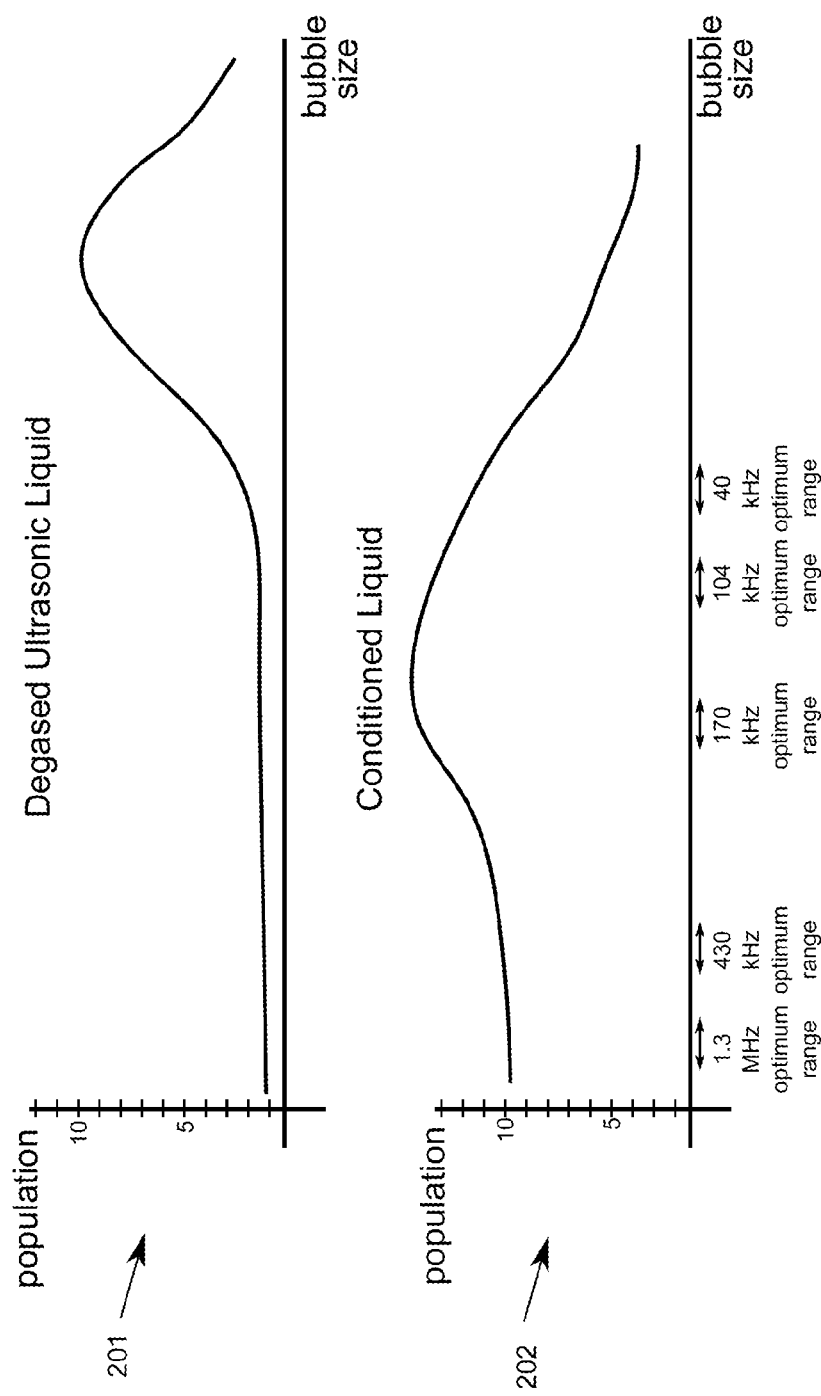
FIG. 5 shows graphs that indicate the shift in bubble size population when the apparatus of FIG. 1 is used to condition the liquid.

More specifically, FIG. 5 compares the bubble size population in a liquid exposed only to sonic energy in graph 201, to the bubble size population in the conditioned liquid in apparatus 100 which has been exposed to both sonic energy and cutting system 102 shown in graph 202. As shown in graph 202, the bubble population has been shifted leftwards, moved to a distribution of smaller bubbles in conditioned liquid. Next, referring to the bubble size range for 430 kHz, shown is that the bubble population in conditioned liquid for 430 kHz in graph 202 is ten times higher than it is in degased ultrasonic liquid in graph 201. Another point shown in graphs 201 and 202 is that the number of bubbles that resonate at 430 kHz is only about one percent of the total bubble population. Also notice the total number of bubbles in the conditioned liquid graph is larger than the total number of bubbles in the degased ultrasonic liquid graph because when you cut larger bubbles into smaller bubbles, the number of bubbles increases.

The conditioned liquid 105 is next passed out of vessel 111 through outlet port 13 to be used by desired sonic processing equipment which will now operate with improved efficiency due to the improved bubble population size profile in the conditioned liquid. After remaining in the external sonic processing equipment for a period of time, the liquid may then be returned to vessel 111 through inlet port 12 for reprocessing.

The conditioned liquid will result in increased cavitation efficiency for many sonic applications. For example, typical ultrasonic cleaning tanks will achieve increased cavitation efficiency when using conditioned liquid generated from apparatus 100.

When a general ultrasound system applies ultrasound to the liquid in the tank, a volume of dissolved gas in the liquid is precipitated as bubbles. Some bubbles are large enough that buoyancy causes the bubbles to rise to the liquid surface and are expelled. However, mid-size to smaller bubbles in the liquid will not have a sufficient buoyant force to overcome viscous fluid friction and Brownian motion to cause the bubbles to rise to the surface in a practicable period of time. Thus, in a typical ultrasound system, a large distribution of bubbles will remain in the liquid.

Bubbles remaining in the fluid may be detrimental or beneficial to the ultrasonic cleaning process based upon their size. More specifically, bubbles of a given size range may act as cavitation nuclei. These cavitation nuclei are beneficial in the ultrasonic cleaning process since the implosion of cavitation nuclei creates shock waves and forces which aid in removing contaminants from surfaces of the object to be cleaned. The bubbles in the desired size range will resonate and continually promote the cleaning process. However, bubbles which are not in the desired size range will hamper the cleaning process. More specifically, bubbles with a size larger than the desired range are not able to act as cavitation nuclei. These bubbles which are larger than the desired range also will disadvantageously absorb ultrasonic energy and convert it directly to heat. By cutting the bubbles that are too large to promote cavitation into smaller bubbles, apparatus 100 is able to produce conditioned liquid. The cavitation efficiency is increased in ultrasound systems that use the conditioned liquid produced in apparatus 100.

In apparatus 100, improved cavitation efficiency conditioned liquid also results with the use of multiple frequency sonic equipment such as the MULTISONIK® system available from Blackstone-NEY Ultrasonics used in apparatus 100. More concretely, the sonic generator waveform or the use of multiple sonic generators at different frequency ranges is utilized to further increase the cavitation efficiency of produced conditioned liquid. The particular bubble size range that is advantageous for promoting cavitation strongly depends upon the particular frequency of the sonic energy applied. This factor is utilized in apparatus 100 to select appropriate sonic waveform steps to increase cavitation efficiency. More specifically, the sonic equipment in apparatus 100 first applies a lower frequency sonic energy to the liquid to both degas the liquid (promote bubble formation) and to cause cavitation to occur. The bubbles created at this low frequency are the desired size range for cavitation at higher frequencies. Apparatus 100 will then be switched to apply sonic energy at the higher frequencies to promote cavitation in the bubbles created by the low frequency sonic energy. At this higher frequency, there are less wrong size bubbles to absorb this higher frequency ultrasonic energy and more right size bubbles to resonate and produce cavitation. However, even with using this state of the art multiple frequency ultrasonic equipment, the ratio of wrong size bubbles to right size bubbles is relatively large. Therefore, maximum cavitation efficiency is achieved with apparatus 100 by the combination of bubble cutting system 102 with the use of multiple frequency sonic waveforms. Therefore, apparatus 100 results in less sonic energy being converted into heat, and a higher cavitation density is achieved.

Other Embodiments

Figure 6:
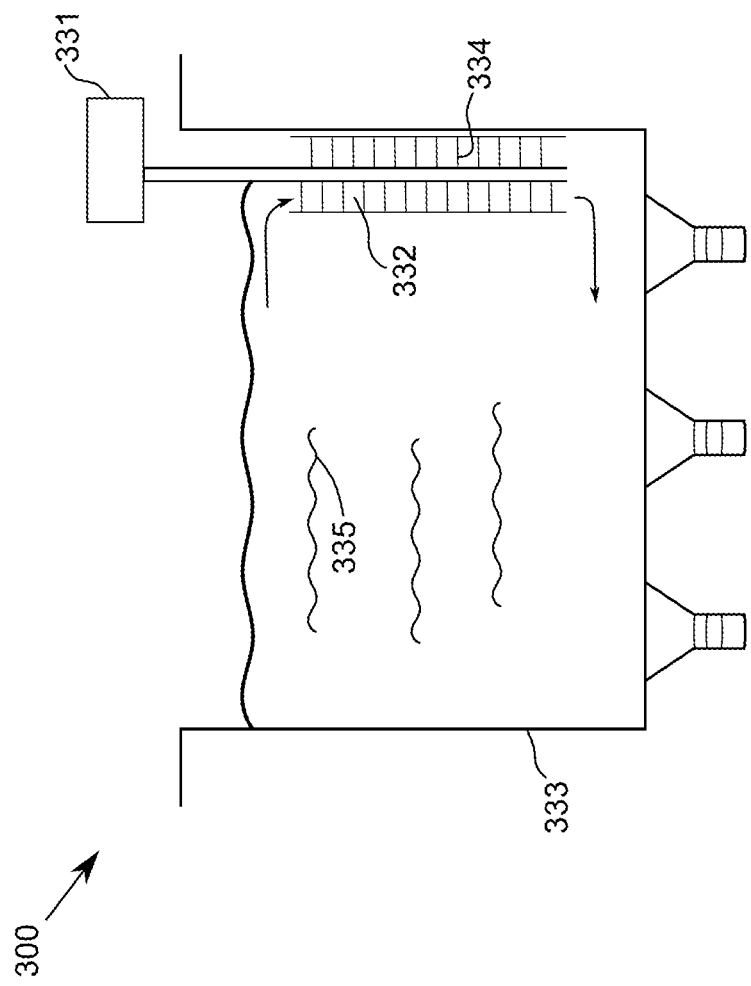
FIG. 6 shows an apparatus of a second embodiment where conditioned liquid is produced within the cleaning or processing vessel.

FIG. 6 shows an apparatus 300 similar to that in FIG. 1 but is built directly into the corner of ultrasonic processing tank 333, instead of being configured to supply an external sonic processing equipment conditioned liquid. In this embodiment, the blades 334 are slightly tilted to cause the liquid 335 to flow into the top of apparatus 332 and down past the blades 334 to be cut and expelled back into the tank near the bottom of apparatus 332. Motor 331 supplies the rotation to the blades for the combination cutting action and downward pumping action. The total apparatus 300 produces high cavitation efficiency because of the shift in bubble population size as detailed in FIG. 4. In alternative versions of apparatus 332, motor 331 may be rotated in the opposite direction to cause a reverse flow where the liquid is pumped by the tilted blades from near the bottom of tank 333 and expelled as conditioned liquid near the top of tank 333.

Figure 7:
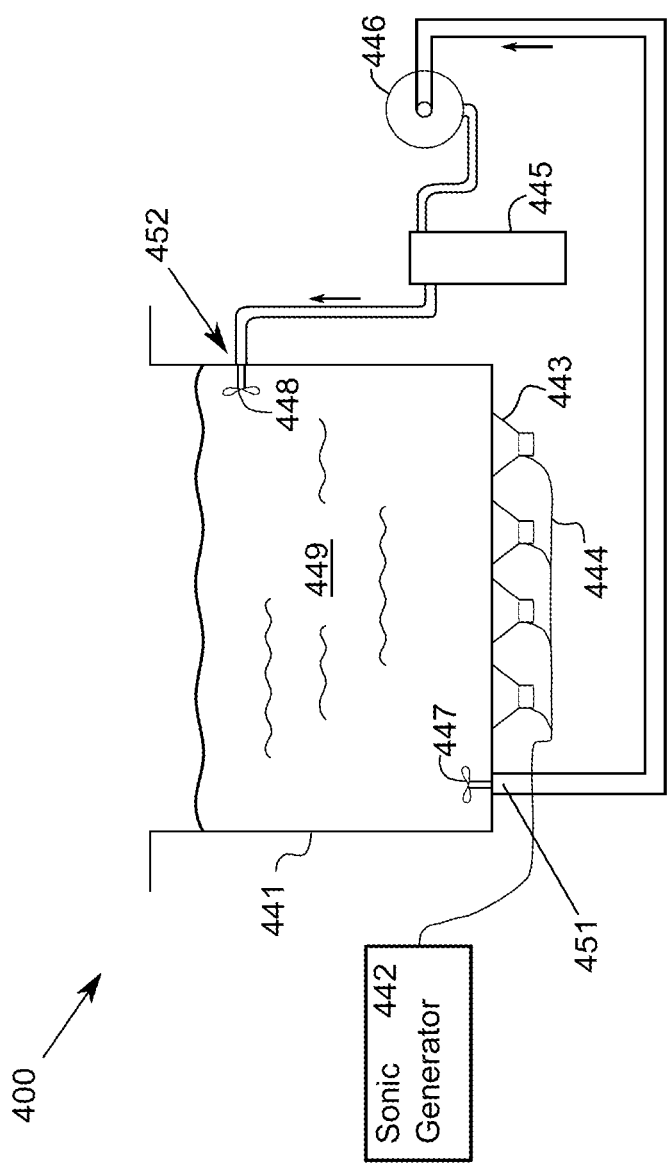
FIG. 7 shows an apparatus of a third embodiment containing a recirculation loop.

FIG. 7 shows next embodiment system 400 which is generally similar to apparatus 300. System 400 has the major components of sonic tank 441 holding liquid 449, transducers 443, cutting blades 447 and 448, pump 446, filter 445, and sonic generator 442. As shown in FIG. 7, transducers 443 are arranged along the bottom of tank 441 and are sonically coupled to liquid 449. Transducers 443 are connected to sonic generator 442 by cable and wires 444. Sonic generator 442 produces a drive frequency typically in the range 20 kHz to 3 MHz usually with state of the art sweeping technology. Blade 447 is arranged on the bottom surface of tank 441 near outlet port 451. Outlet port 451 is in fluid communication with a pipe which leads to pump 446. The flow path through pump 446 continues through filter 445. The flow from filter 445 continues to inlet port 452 in the right side wall of tank 441. Adjacent to inlet port 452 on the inside of tank 441 is blade 448.

The drive frequencies used by sonic generator 442 results in cavitation in liquid 449. A recirculation loop is formed starting and ending at tank 441 and following the flow path of first passing by blades 447, outlet port 451, pump 446, filter 445, and inlet port 452 which completes the loop to tank 441. Blades 447 and 448 spin as liquid passes them due to the pump flow. The bubbles in the liquid released by the sonic field in the tank 41 are cut by blades 447 and 448 into smaller bubbles. This population of smaller bubbles results in improved efficiency and higher cavitation density in the liquid 449. It is clear to one skilled in the art that system 400 may function with only one set of blades, either 447 or 448, but that increased performance is achieved with both sets of blades in place.

Figure 8:
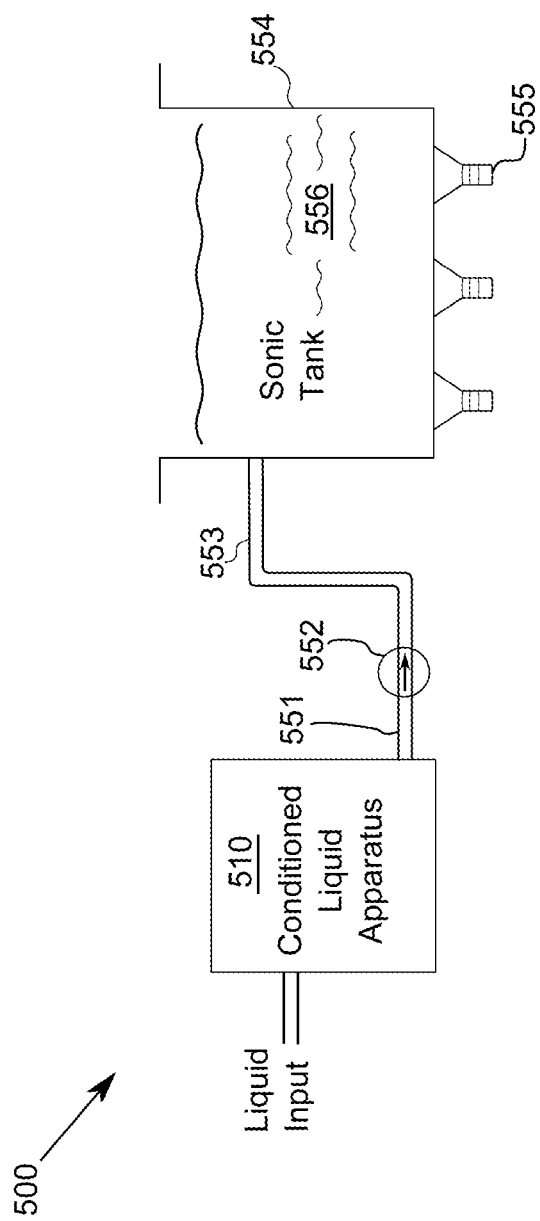
FIG. 8 shows an apparatus of the two vessel embodiment.

FIG. 8 shows next embodiment system 500 where liquid flows into conditioned liquid apparatus 510. After conditioning as described for FIG. 1, the liquid is pumped by way of line 551, pump 552 and line 553 into sonic tank 554. Transducers 555 couple sonic energy into liquid 556 where improved sound efficiency and higher cavitation density occur because of the improved bubble population of the conditioned liquid that was supplied to tank 554.

Figure 9:
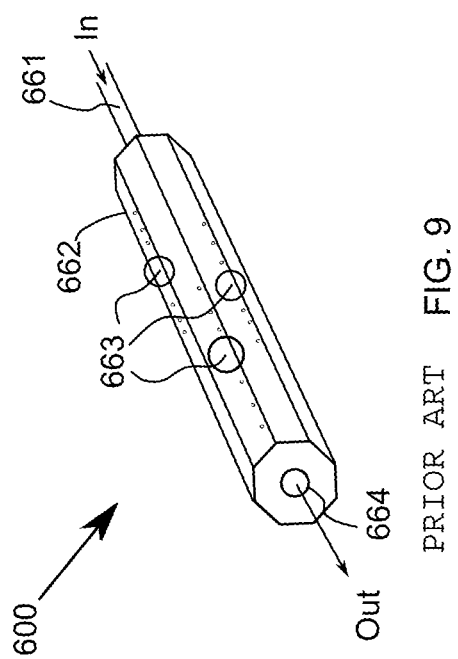
FIG. 9 shows a prior art apparatus for producing high cavitation density.

FIG. 9 shows a high cavitation density flow through sonic vessel 600 that is well known in the art. Liquid flows into port 661 and is exposed to a strong sonic field in chamber 662 by the many transducers 663 that couple sonic energy into chamber 662 from every angle along the total length of the regular polygon shaped vessel. The three dots before and after each transducer 663 depict many transducers along the total length of the polygon face. Output port 664 is where the liquid exits after being exposed to the high energy sonic field in system 600.

Figure 10:
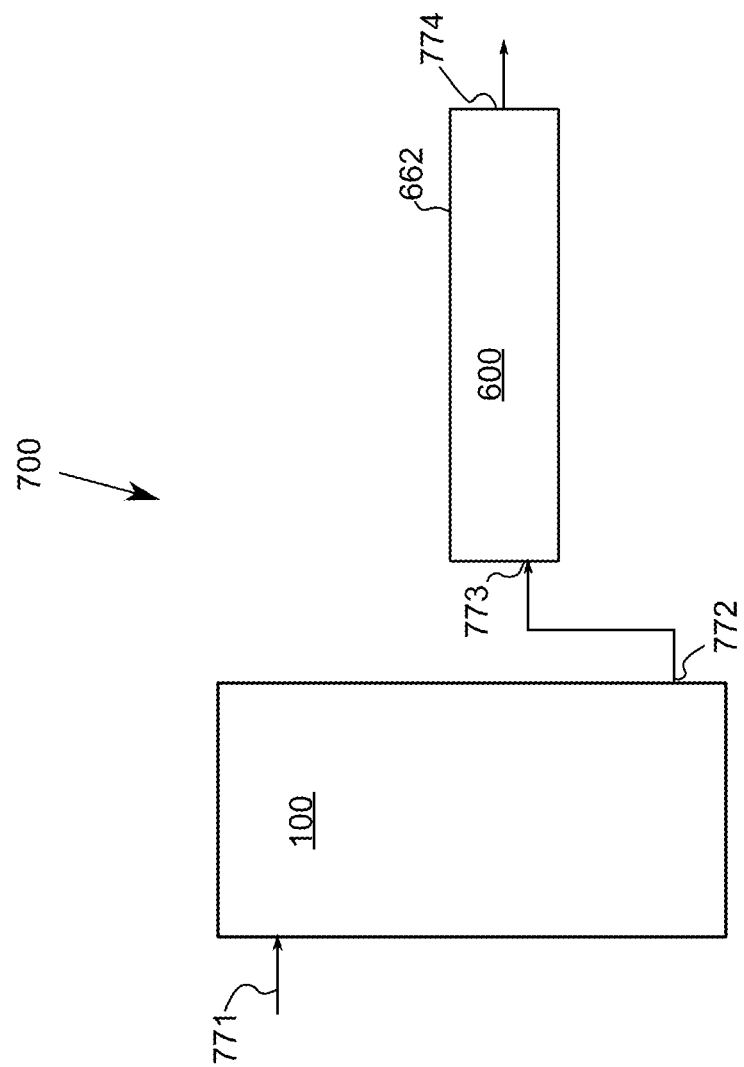
FIG. 10 shows a flow diagram of an apparatus of a continuous flow processing system embodiment.

FIG. 10 shows system 700 consisting of system 100 for producing conditioned liquid and system 600 for delivering a high energy sonic field to the conditioned liquid. Liquid flows into system 100 at 771 and the conditioned liquid with a shifted bubble population similar to that shown in the conditioned liquid graph of FIG. 4 flows out at 772. This conditioned liquid flows into system 600 at 773 and is exposed to very high cavitation density in vessel 662 because of the increased efficiency of sonic energy in conditioned liquid. The liquid that flows out at 774 has experienced high cavitation density which has many useful effects such as a high rate of organism inactivation.

Another technique to increase the bubble population of smaller right size bubbles is to add microorganisms, for example yeast, that produce bubbles as they feed, grow and reproduce. These bubbles will increase cavitation density and is useful for applications where the microorganisms are not a contaminant to the process.

Figure 11:
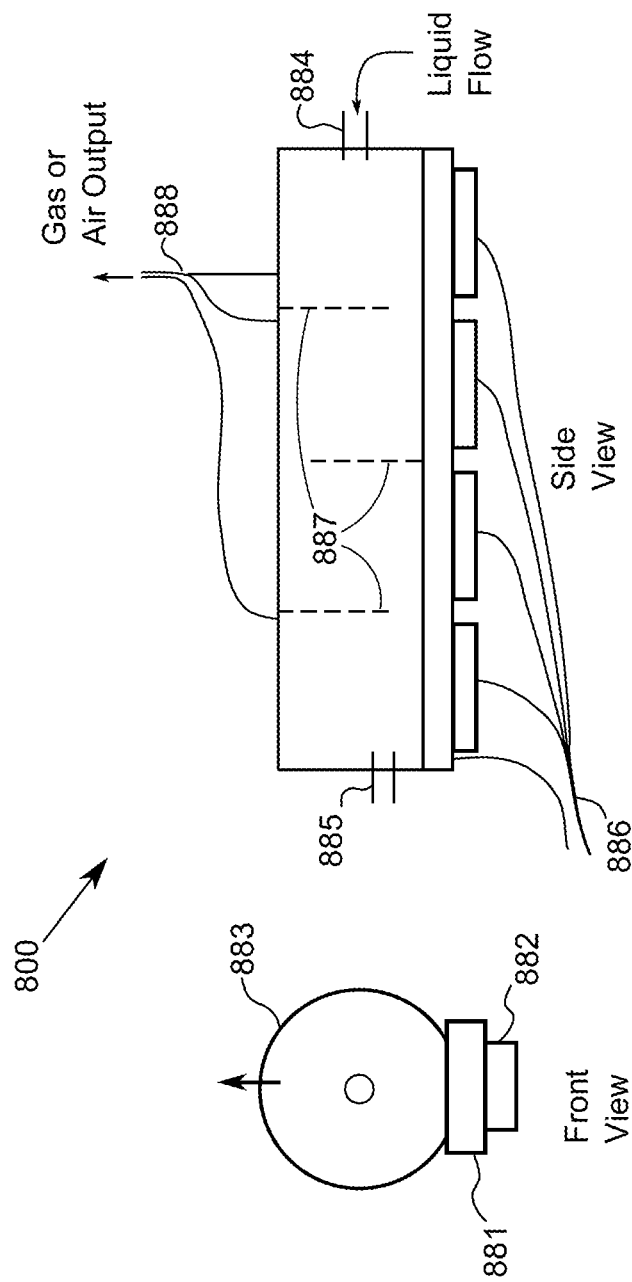
FIG. 11 shows an apparatus used for targeting specific size organisms.

FIG. 11 shows an apparatus designed for targeting organisms or other discontinuities in the liquid with a specific frequency or frequency range related to the target size. As explained later in FIGS. 12, 15, 16, and 17, there is a relationship between frequency and target size and the proper frequency for a specific target can be determined by methods taught later in this specification. Those methods involve finding the frequency that causes the target to become a nucleus of cavitation where a transient cavitation event occurs or where stable cavitation occurs. The apparatus 800 in FIG. 11 is designed to supply the frequency or frequency range related to the target. Apparatus 800 is particularly useful for targets below about 15 microns in size because megasonic frequencies generally are required.

Plate 881 and case 883 form the tubular vessel into which sonic energy is transmitted by transducers 882 driven through cable 886 by a generator (not shown). The plate 881 is designed to match the piezoelectric transducer 882 at the design frequency determined to cause the target to act as a cavitation nucleus. This design technique requires the thickness of the plate have an integer number of half wavelengths of sound at the design frequency and the piezoelectric ceramic has an odd integer number of half wavelengths of sound at the design frequency. The side view in FIG. 11 shows the vessel 883 with baffles 887 to make the path of the liquid longer through the apparatus. The baffles are not required for a working apparatus, but they improve its performance. Also in the side view is shown the liquid input port 884 and output port 885 and escape tubing 888 for gas or air released from the liquid.

Figure 12:
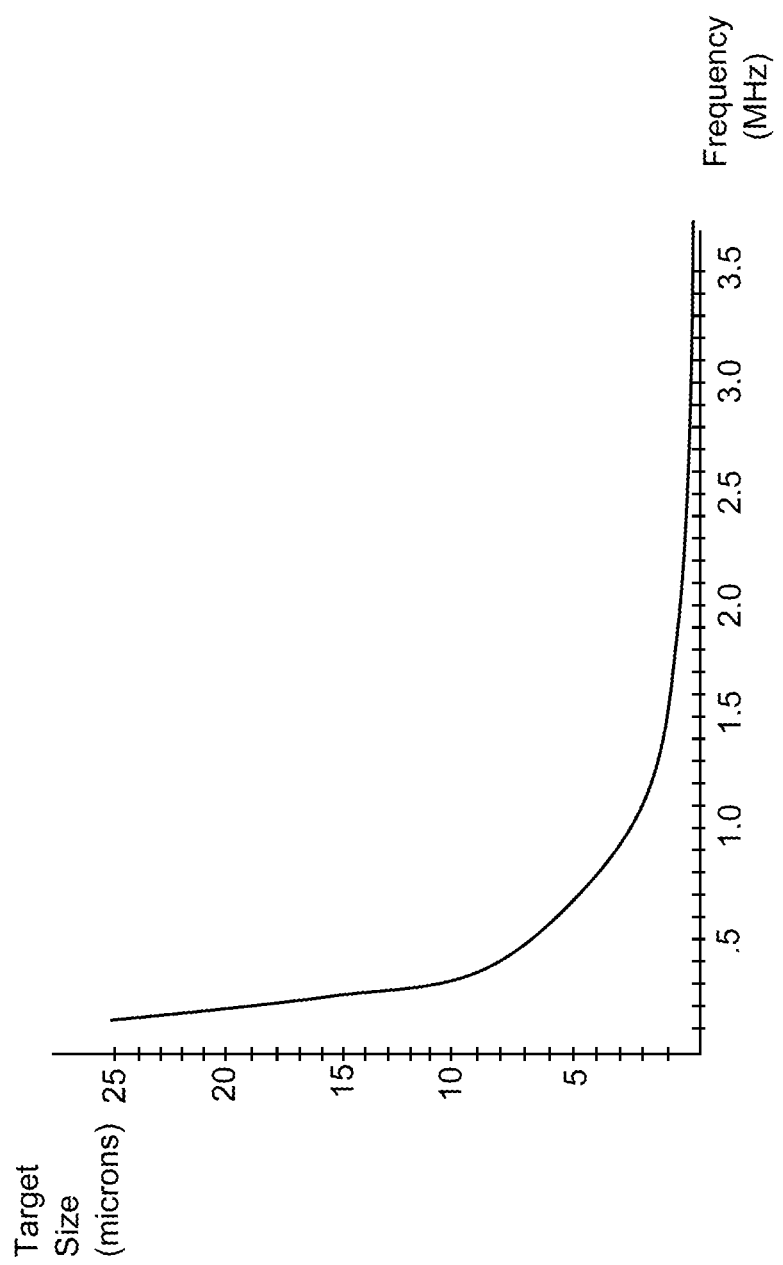
FIG. 12 shows a graph with a relationship of target size versus sonic frequency for causing targets to act as cavitation nuclei.

FIG. 12 shows a graph with a relationship of target size versus sonic frequency for causing targets to act as cavitation nuclei. The relationship shown in FIG. 12 is only a general guideline because the specific relationship between the target and frequency will vary depending on the target and liquid characteristics.

Figure 13:
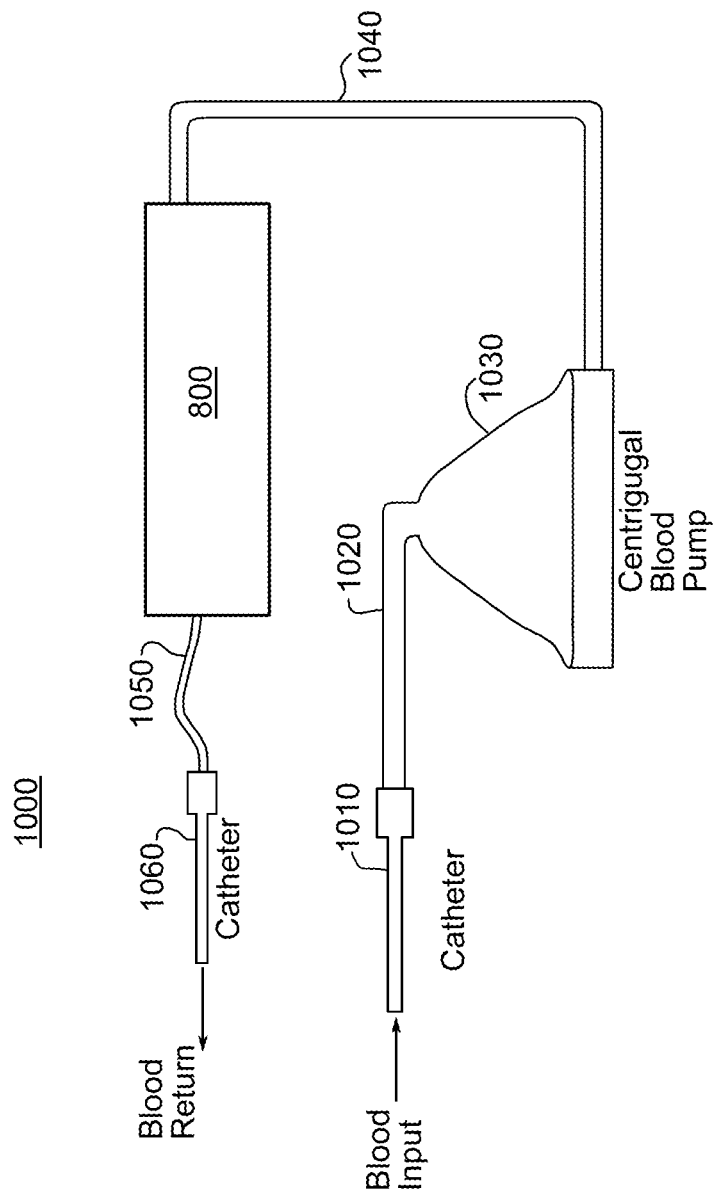
FIG. 13 shows an apparatus for targeting cancer cells in blood.

FIG. 13 shows system 1000, an apparatus for targeting and destroying cancer cells in blood while leaving healthy cells virtually unharmed. Catheter 1010 is inserted into a vein to draw blood from the body. The blood flows into catheter 1010 through tube 1020 to centrifugal blood pump 1030 because of the suction of pump 1030. The output of pump 1030 forces the blood through tube 1040 into apparatus 800 from FIG. 11. This apparatus is designed with the frequency or frequency range determined to be that which causes the cancer cells to become cavitation nuclei. The design procedure is explained in the FIG. 11 paragraph above and the frequency determination is guided by FIG. 12 with specific empirical determination of frequency as taught in the follow on paragraphs about FIGS. 15 and 16 below. The blood with destroyed cancer cells leaves apparatus 800 in tube 1050 and is returned to the body by catheter 1060.

Figure 14:
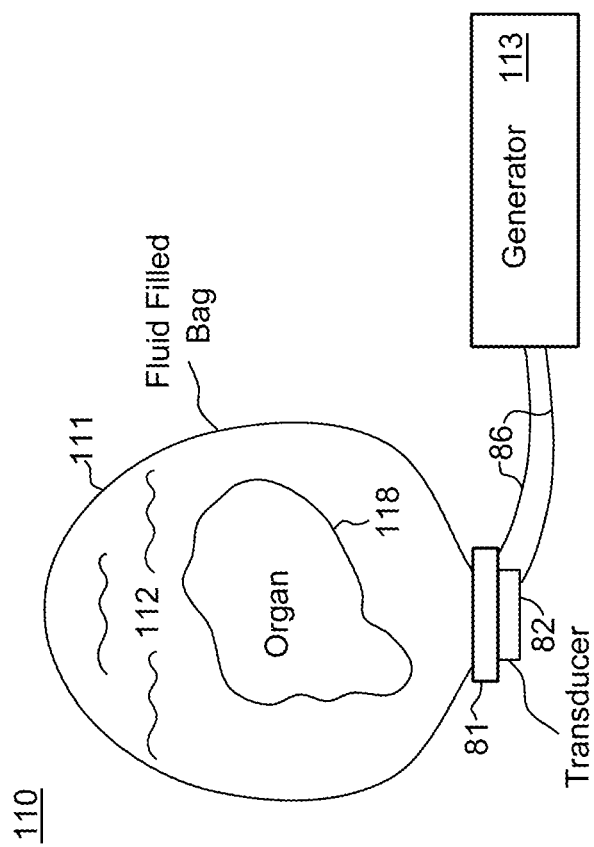
FIG. 14 shows an apparatus for destroying cancer cells in an organ.

FIG. 14 shows a system 110 for destroying cancer cells in an organ by causing the cancer cells to become cavitation nuclei. Cancer cells are generally a different size than healthy cells, therefore, using the teachings in this specification the frequency or frequency range that resonates the cancer cells and causes the cancer cells to become cavitation nuclei is found, call this range of frequencies Fr. The piezoelectric ceramic transducer 82 and plate 81 are designed to work at Fr by techniques well known to megasonic engineers and as briefly described in the paragraph on FIG. 11. The generator 113 is designed and tuned to produce an electrical drive signal at Fr which is transmitted through cable 86 and drives piezoelectric ceramic 82 at Fr. This couples sonic energy at Fr into liquid 112 which surrounds the organ 118. The coupling liquid is held in place by bag 111. During the operation of system 110, the proper frequency Fr is coupled into liquid 112 which transmit the Fr sound waves to organ 118. The cancer cells in organ 118 resonate with the application of sound waves at Fr and become cavitation nuclei. The cancer cells either transient cavitate and are destroyed by their implosion or they may undergo stable cavitation, the distortion of which inactivates the cancer cells. Because the healthy cells are generally a different size than the cancer cells, Fr does not resonate the healthy cells and they are left virtually unharmed.

Figure 15:
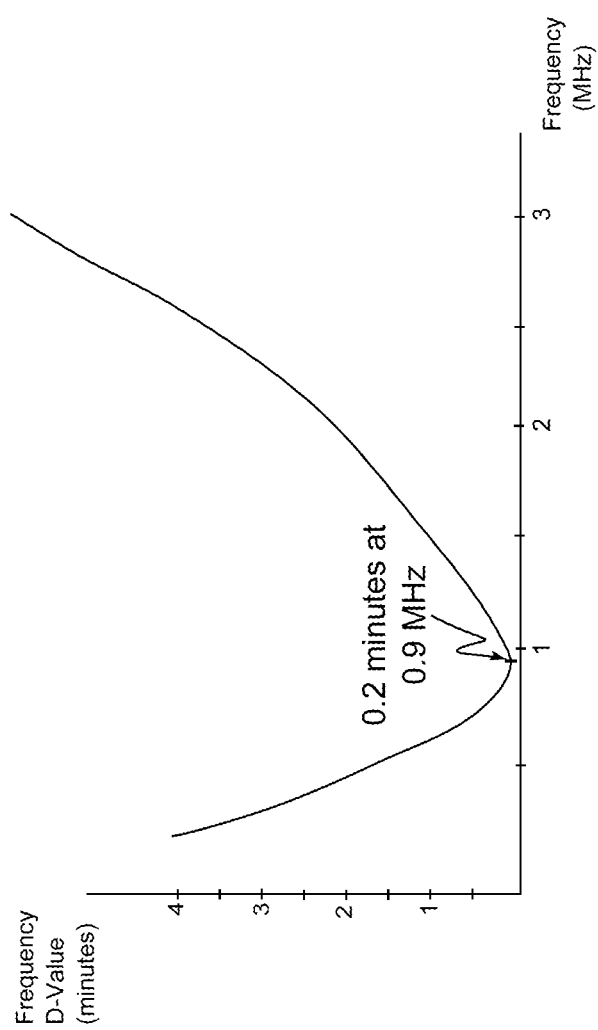
FIG. 15 shows a graph with a relationship of frequency D-value versus frequency for organisms.

FIG. 15 is an example of a graph that results when empirically determining the proper frequency to cause a particular organism to become a cavitation nucleus. The procedure is as follows: a sample liquid containing the organism of interest is subjected to a chosen frequency or range of frequencies around the chosen frequency (state of the art ultrasonic and megasonic equipment sweep frequency, for example, if the chosen frequency is 1.4 MHz, the actual frequency will constantly be changed within the frequency range 1.39 MHz to 1.41 MHz). By techniques well known to microbiologists, a frequency D-value is determined at the chosen frequency, i.e., the time of exposure to the chosen frequency needed to reduce the initial organism count by 90 percent. This time is plotted on the y-axis as a function of frequency on the x-axis as shown in FIG. 15. A second chosen frequency is supplied to the sample liquid containing the organisms of interest. The frequency D-value is determined for this second chosen frequency. This D-value is plotted on the graph. The process is continued until a minimum point is identified on the plot. As an example, in FIG. 15 the minimum point was found to be at 0.9 MHz. To cavitate these organisms of interest, the system supplying the sonic energy would typically be designed to supply a sweeping frequency within the frequency range 0.89 MHz to 0.91 MHz.

Figure 16:
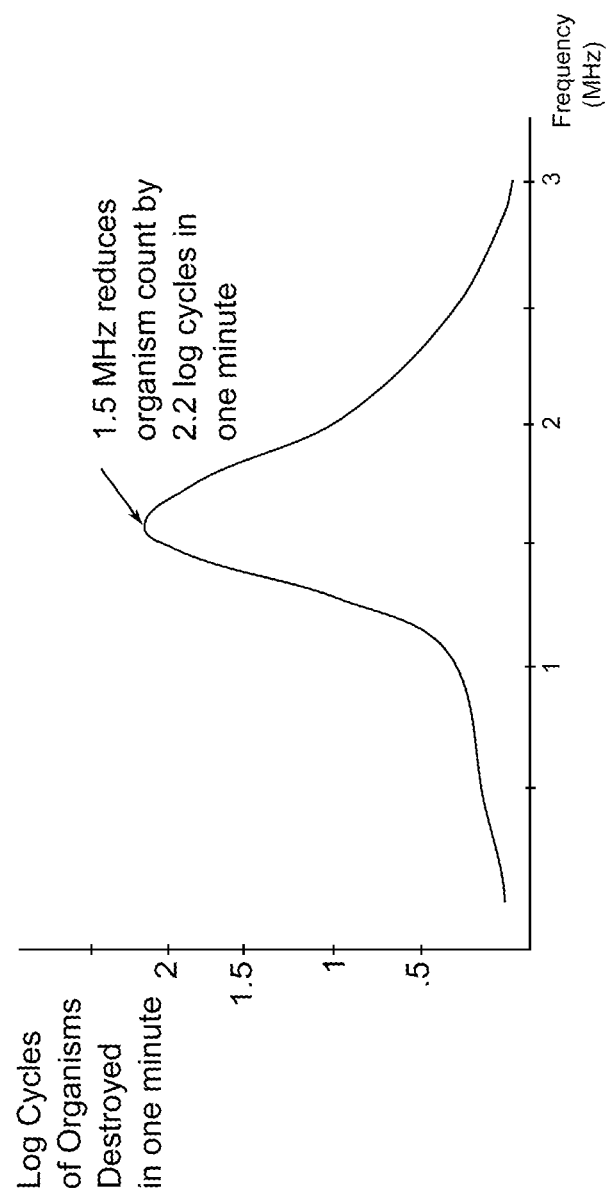
FIG. 16 shows a graph with a relationship of log cycles of organisms destroyed versus frequency.

FIG. 16 is an example of a graph that results when empirically determining the proper frequency to cause a particular organism to become a cavitation nucleus. This method is quicker to accomplish that the method for FIG. 15 because only one measurement is necessary for each data point. A data point on the graph is determined in the following way. Take a sample of the liquid containing the target organisms and do a set of cultures to determine the initial organism count. Expose the liquid containing the target organisms for a fixed time (in this example the fixed time is one minute) to a selected frequency or sweeping frequency range (if a sweeping frequency range is used, the center frequency of the range is plotted on the FIG. 16 graph). Culture the exposed sample to determine the number of log cycles reduction in organism count. This is done by dividing the initial count by the exposed count and taking the log to the base 10 of that number. In the FIG. 16 example, it is shown that the maximum log cycle reduction occurred at 1.5 MHz, this reduction was 2.2 log cycles.

Figure 17:
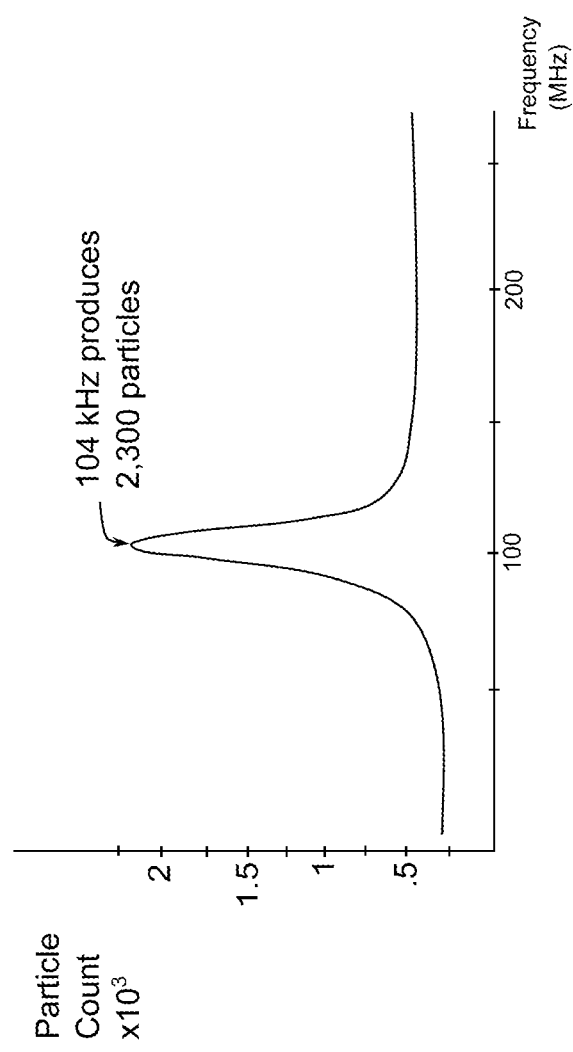
FIG. 17 shows a graph with a relationship of particle count versus frequency for targets.

FIG. 17 shows a graph of a technique used to determine the proper drive frequency for imploding structures that are not living. When these microstructures are exposed to the proper frequency that causes them to be cavitation nuclei, they are imploded into nanostructures increasing the particle count. A particle counter is used to determine the particle count for each frequency data point. The data is plotted as shown in FIG. 17 and the peak value gives the proper frequency, in this example it is 104 kHz.

Figure 18:
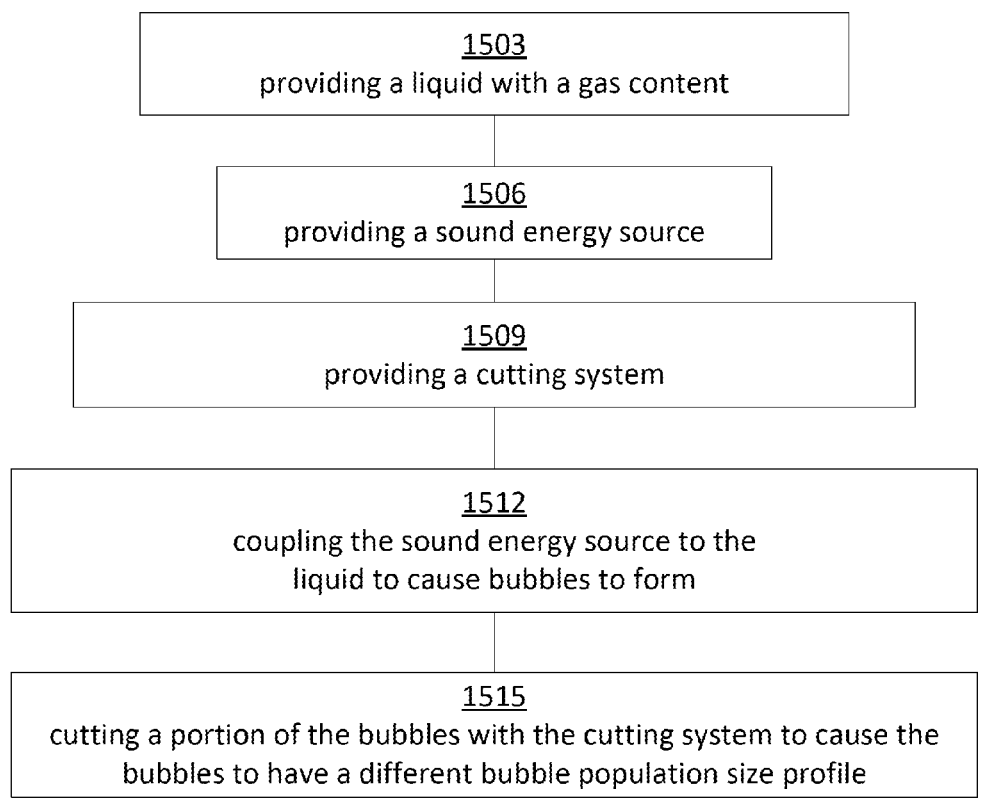
FIG. 18 is a flow chart of an embodiment method.

FIG. 18 is a flow chart of embodiment method 1500 of conditioning a liquid for sonic applications. Method 1500 has the steps of providing a liquid with a gas content 1503, providing a sound energy source 1506, providing a cutting system 1509, coupling the sound energy source to the liquid to cause bubbles to form 1512, and cutting a portion of the bubbles with the cutting system to cause the bubbles to have a different bubble population size profile 1515.

Figure 19:
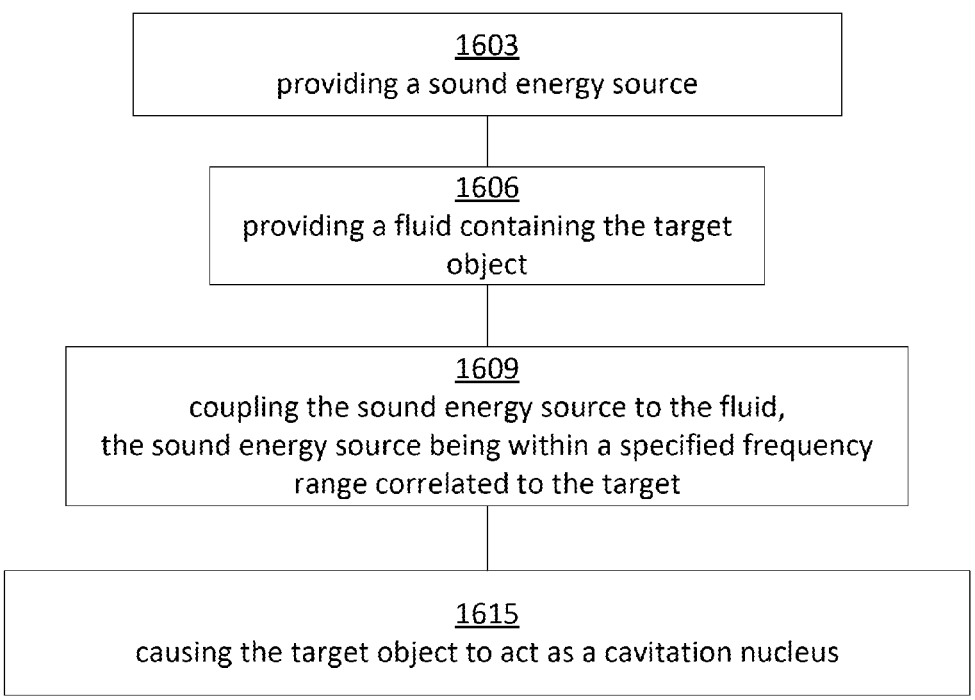
FIG. 19 is a flow chart of another embodiment method.

FIG. 19 is a flow chart of embodiment method 1600 of causing a target object to act as a cavitation nucleus. Method 1600 has the steps of providing a sound energy source 1603, providing a fluid containing the target object 1606, coupling the sound energy source to the fluid 1609, in which the sound energy source is within a specific frequency range that resonates the target, to cause the target object to act as a cavitation nucleus 1615.

Figure 20:
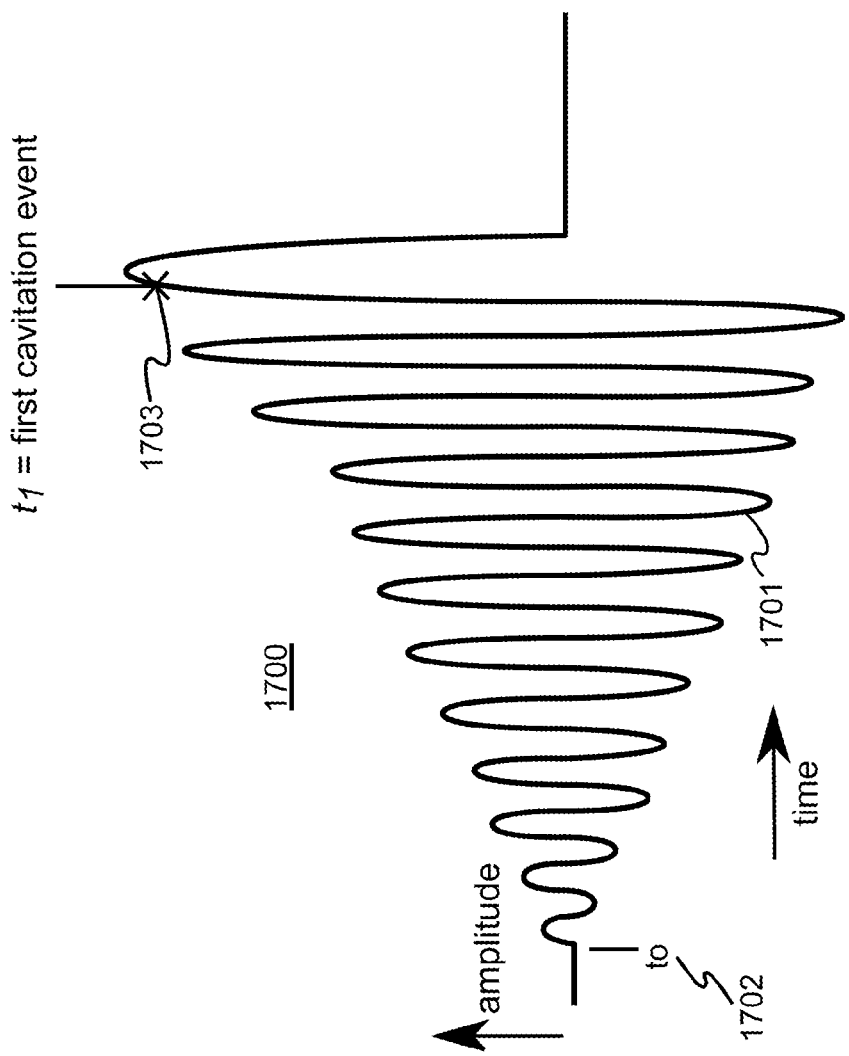
FIG. 20 shows an example of a monotonically increasing sound energy waveform for producing high energy density cavitation at a known time.

FIG. 20 shows graph 1700 which is an example of a monotonically increasing sound energy waveform 1701 for producing high energy density cavitation at a known time, t1, 1703. The amplitude envelope starting at t0, 1702, of the sound energy produced may be varied in a method to encourage high energy density events to occur. More specifically, the amplitude of the sound energy produced may be characterized by monotonically increasing amplitude prior to the onset of cavitation 1703. In particular, using a sonic generator which provides an exponentially increasing amplitude is deemed to increase the chances that high energy density events will occur.

Figure 21:
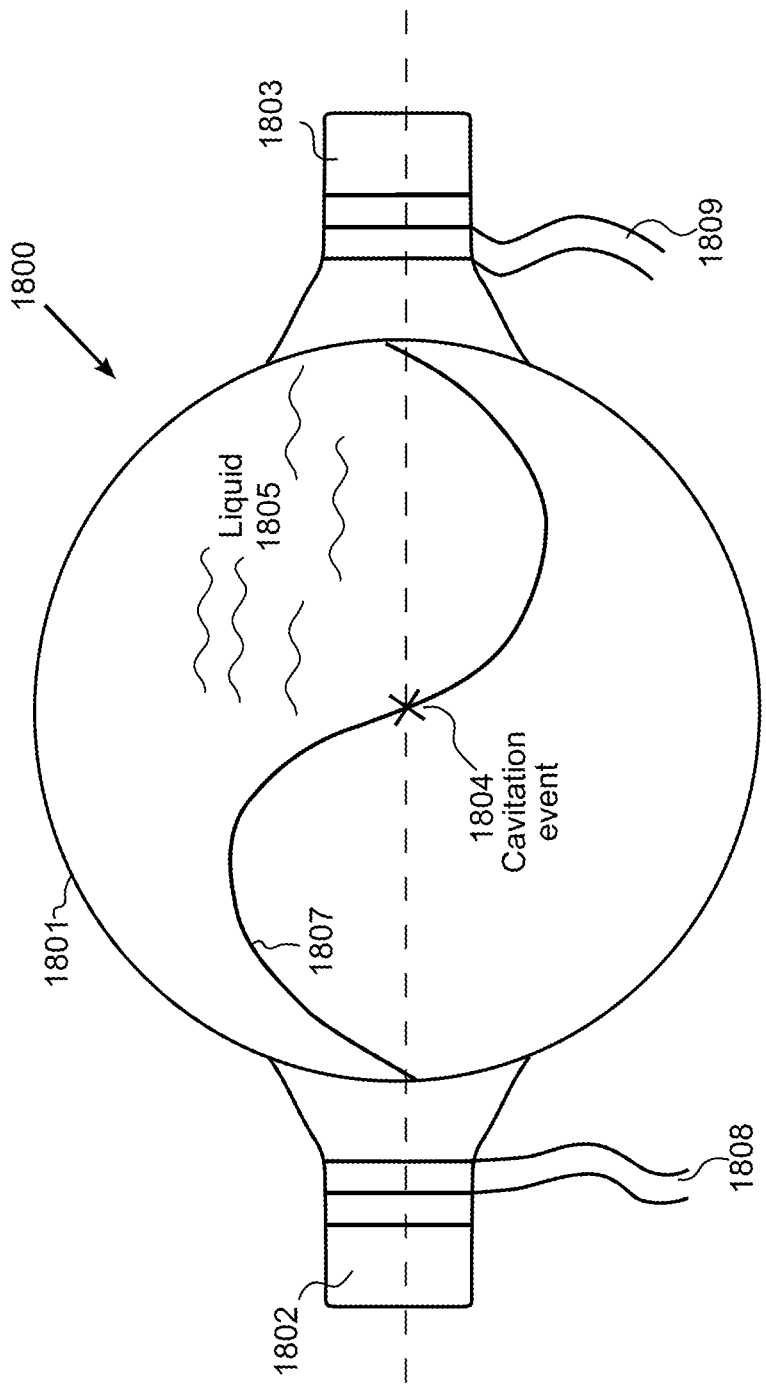
FIG. 21 shows a cross-section of a spherical chamber where sound waves are focused at its center to produce a high energy density event in a known location.

Additionally, the chance of producing high energy events may be further improved by providing a tank or chamber 1801 with liquid 1805 as shown in FIG. 21 where the sonic energy 1807 is focused at 1804. Such a tank or chamber 1801 with transducers 1802 and 1803 driven by a sonic generator (not shown) connected to leads 1808 and 1809 may also provide a synchronization signal to an additional energy source, for example, an electric current, a neutron source, or a laser or lasers (not shown) which direct a burst of energy at a cavitation implosion 1804 to increase the energy density within the cavitation event 1804.

Further, the apparatus 1800 may also provide tracking of a three dimensional location (center of spherical chamber) and time (t1, 1703 in FIG. 20) of a cavitation event in order to allow precise application of additional energy for increasing the energy density of the cavitation event 1804.

These improvements can be tuned to produce a single high energy cavitation event in a known location and at a known time or alternatively, the system can be slightly detuned to produce a cloud of multiple high energy cavitation events.

The disclosed embodiments may be embodied in other specific forms without departing from its spirit or essential characteristics. The present embodiments are therefore to be considered as illustrative and not restrictive, the scope of the disclosed embodiments being indicated by the appended claims rather than by the foregoing description, and all changes which come within the meaning and range of the equivalency of the claims are therefore intended to be embraced therein. Accordingly, while the presently-preferred forms of the system have been shown and described, and several embodiments discussed, persons skilled in this art will readily appreciate that various additional changes and modifications may be made without departing from the spirit of the invention, as defined and differentiated by the following claims.

The invention claimed is:

1. A method of causing cancer cells in blood of a patient to act as cavitation nuclei, comprising the steps of:
   sequentially depositing a plurality of test blood samples from the patient with first cancer cells in a single chamber;
   exposing each of said test blood samples, when in the single chamber, to sound energy at a different respective one of a plurality of sweeping frequencies generated by a sound energy source, wherein the entire volume of each of said test blood samples is exposed;
   determining an inactivation efficiency of the first cancer cells for each of said test blood samples;
   determining a resonant sweeping frequency that (a) within the range spanned by the plurality of sweeping frequencies, optimally destroys the first cancer cells and (b) has center frequency in the range 350 kHz to 15 MHz and sweep frequency bandwidth between 0.1 percent and 7 percent of the center frequency;
   circulating the blood of the patient out of the patient via a first catheter, through a vessel coupled with a second sound energy source, and back into the patient through a second catheter; and
   exposing the blood to sound energy generated by the second sound energy source at said resonant sweeping frequency to cause second cancer cells in the blood and of same type as the first cancer cells to act as cavitation nuclei and implode while untargeted cells in the blood remain viable, wherein the entire volume of the blood contained by said vessel is exposed to said resonant sweeping frequency.

2. The method as set forth in claim 1, wherein said inactivation efficiency comprises a measure of an exponential rate of decrease in the number of active cancer cells remaining.

* * * * *